(12) United States Patent
Provost et al.

(10) Patent No.: US 7,072,842 B2
(45) Date of Patent: Jul. 4, 2006

(54) PAYMENT OF HEALTH CARE INSURANCE CLAIMS USING SHORT-TERM LOANS

(75) Inventors: Wayne A. Provost, Salt Lake City, UT (US); Brian E. Peterson, Salt Lake City, UT (US)

(73) Assignee: P5, Inc., Salt Lake City, UT (US)

( * ) Notice: Subject to any disclaimer, the term of this patent is extended or adjusted under 35 U.S.C. 154(b) by 1105 days.

(21) Appl. No.: 09/756,077

(22) Filed: Jan. 8, 2001

(65) Prior Publication Data

US 2002/0091549 A1 Jul. 11, 2002

(51) Int. Cl.
  *G06F 19/00* (2006.01)
  *G06Q 10/00* (2006.01)
  *G06Q 40/00* (2006.01)

(52) U.S. Cl. ............................. 705/4; 705/2; 705/35

(58) Field of Classification Search ................ 705/2–4, 705/39, 35, 36 R, 36 T
See application file for complete search history.

(56) References Cited

U.S. PATENT DOCUMENTS

| | | | | |
|---|---|---|---|---|
| 4,491,725 A | * | 1/1985 | Pritchard | 705/2 |
| 4,831,526 A | | 5/1989 | Luchs et al. | 364/401 |
| 4,858,121 A | | 8/1989 | Barber et al. | 364/406 |
| 4,876,648 A | * | 10/1989 | Lloyd | 705/38 |
| 4,890,228 A | * | 12/1989 | Longfield | 705/31 |
| 5,025,138 A | * | 6/1991 | Cuervo | 705/38 |
| 5,193,057 A | * | 3/1993 | Longfield | 705/31 |
| 5,225,976 A | | 7/1993 | Tawil | 364/401 |
| 5,235,507 A | * | 8/1993 | Sackler et al. | 705/2 |
| 5,253,164 A | | 10/1993 | Holloway et al. | 364/406 |
| 5,301,105 A | | 4/1994 | Cummings, Jr. | 364/401 |
| 5,359,509 A | * | 10/1994 | Little et al. | 705/2 |
| 5,426,281 A | * | 6/1995 | Abecassis | 235/379 |
| 5,519,607 A | | 5/1996 | Tawil | 364/401 |
| 5,523,942 A | | 6/1996 | Tyler et al. | 364/401 |
| 5,644,778 A | * | 7/1997 | Burks et al. | 705/2 |
| 5,704,044 A | | 12/1997 | Tarter et al. | 395/204 |
| 5,903,873 A | | 5/1999 | Peterson et al. | 705/4 |

(Continued)

FOREIGN PATENT DOCUMENTS

JP  2003022410 A  *  1/2003

OTHER PUBLICATIONS

Claimsnet.com, accessed at archive.org, Apr. 11, 1997 archive date.*

(Continued)

*Primary Examiner*—Joseph Thomas
*Assistant Examiner*—Carolyn Bleck
(74) *Attorney, Agent, or Firm*—Workman Nydegger (57) ABSTRACT

Methods and systems for promptly paying health care providers for rendered health care services. A medical technician operating a client computer establishes communication with a remote server. Using a claim form, the technician enters patient, insurance, and treatment information which is transmitted to the server to determine whether the claim is eligible for advance payment. If the claim is eligible, the server transmits claim information to an appropriate carrier for claim processing. The remote server also transmits claim information to a payment entity which requests from a financial entity that funds be credited to an operational account and a reserve account. The funds of the operational account are immediately accessible to the health care provider. The funds of the reserve account are debited for expenses. When the carrier finally processes the claim, any payment for the claim is deposited into the reserve account.

32 Claims, 3 Drawing Sheets

U.S. PATENT DOCUMENTS

| | | | |
|---|---|---|---|
| 5,903,881 A * | 5/1999 | Schrader et al. | 705/42 |
| 5,911,132 A | 6/1999 | Sloane | 705/3 |
| 5,915,241 A | 6/1999 | Giannini | 705/2 |
| 5,930,759 A | 7/1999 | Moore et al. | 705/2 |
| 5,953,710 A * | 9/1999 | Fleming | 705/38 |
| 5,963,921 A * | 10/1999 | Longfield | 705/31 |
| 6,003,007 A | 12/1999 | DiRienzo | 705/4 |
| 6,012,035 A * | 1/2000 | Freeman et al. | 705/2 |
| 6,029,150 A * | 2/2000 | Kravitz | 705/39 |
| 6,112,183 A | 8/2000 | Swanson et al. | 705/2 |
| 6,202,052 B1 * | 3/2001 | Miller | 705/31 |
| 6,208,973 B1 * | 3/2001 | Boyer et al. | 705/2 |
| 6,304,860 B1 * | 10/2001 | Martin et al. | 705/43 |
| 6,477,513 B1 * | 11/2002 | Walker et al. | 705/76 |
| 6,820,058 B1 * | 11/2004 | Wood et al. | 705/4 |
| 2001/0047329 A1 * | 11/2001 | Ashby | 705/39 |
| 2002/0002475 A1 * | 1/2002 | Freedman et al. | 705/4 |
| 2002/0004782 A1 * | 1/2002 | Cincotta | 705/39 |
| 2002/0010685 A1 * | 1/2002 | Ashby | 705/80 |
| 2002/0087461 A1 * | 7/2002 | Ganesan et al. | 705/39 |
| 2002/0087465 A1 * | 7/2002 | Ganesan et al. | 705/39 |
| 2002/0087469 A1 * | 7/2002 | Ganesan et al. | 705/40 |
| 2002/0147678 A1 * | 10/2002 | Drunsic | 705/39 |
| 2003/0187695 A1 * | 10/2003 | Drennan | 705/2 |
| 2004/0002915 A1 * | 1/2004 | McDonald et al. | 705/38 |
| 2004/0083185 A1 * | 4/2004 | Currans et al. | 705/77 |
| 2004/0236613 A1 * | 11/2004 | Lundberg | 705/4 |
| 2005/0033677 A1 * | 2/2005 | Birdsong et al. | 705/35 |
| 2005/0216315 A1 * | 9/2005 | Andersson | 705/4 |

OTHER PUBLICATIONS

Overman, William and William McCormick, Setting Up a Law Practice, Practical Lawyer, v. 42, n.5, pp. 35-46, Jul. 1996 File # 485, #00582784.*

Sean P. Sweeney, Murphy's Law in Different Cases, Lawyer's Fee Structures Vary, Patriot Ledger, Jun. 27, 1998, File # 781, #03506094.*

Llana, Jr. A. 'Conveying the Image', Feb. 1992, v12, n8, p. 22 (4). Gale Group Computer DB [online] DG Review. Retrieved from: Dialog Accession No. 01513428.

'Octel unveils strategic roadmap for health care marketplace focus is on efficiency-enhancing applications global messaging' Mar. 1996, Gale Group, Retrieved from: Dialog Accession No. 01354156.

Tanner, Lisa Claimsnet files to IPO to fund Internet service Dallas Business Journal, May 8, 1998, vol. 21 Issue 37, p. 10, 1/2 p.

Hagland, Mark Healtheon: Zigging and zagging to adjust to health care realities Health Management Technology; Atlanta; Jul. 1997 vol. 18, Issue 18, p. 30.

* cited by examiner

Health Care Claims Form — 12a

| Plan I D | |
|---|---|
| Insured's I D | |
| Paitent's date of birth | - mm/dd/yy |
| Provider I D | |

Labels: 26, 34, 38, 36

FIG. 3

Health Care Claims Form — 12b

50 {
- Plan ID : 1234
- Insured : Doe, John 541XXXXX
- Patient : 01, Jane
- Provider: MISCELLANEOUS PROVIDERS

| Please enter the Patient Dependent Number from above from above: | | | | | | |
|---|---|---|---|---|---|---|
| Last Name, First, Middle Initial, I.D. | | | | | | |
| Referring Physician | | | | | | |
| Service Provider | | | | | | |
| Diagnosis or Nature of Illness or Injury. | | | | | | |

52, 52, 56

| Dates of Service | | Place | Type | Procedure, Service or Supplies | | | $Charges |
|---|---|---|---|---|---|---|---|
| From | To | Svc | Svc | CPT | Modifier | Diagnosis No | |
| | | | | 54 | | | |
| | | | | | | | |
| | | | | | | | |
| | | | | | | | |
| | | | | | | | |

60

| Patient's Account | Accept Assign? | Total Charge | | 62 |
|---|---|---|---|---|
| | Yes O   No O | Amount Paid | | 58 |
| | | Balance Due | | 64 |

FIG. 4

PAYMENT OF HEALTH CARE INSURANCE CLAIMS USING SHORT-TERM LOANS

BACKGROUND OF THE INVENTION

1. The Field of the Invention

The present invention relates to systems and methods for approving and paying health care insurance claims promptly. More particularly, the present invention relates to systems and methods for promptly paying health care providers for services rendered before the health care insurance claims can be processed and, if necessary, adjudicated by an associated carrier or payer.

2. Relevant Technology

The cost of health care continues to increase as the health care industry becomes more complex, specialized, and sophisticated. The proportion of the gross domestic product that is accounted for by health care is expected to gradually increase over the coming years as the population ages and new medical procedures become available. Over the years, the delivery of health care services has shifted from individual physicians to large managed health maintenance organizations. This shift reflects the growing number of medical, dental, and pharmaceutical specialists in a complex variety of health care options and programs. This complexity and specialization has created large administrative systems that coordinate the delivery of health care between health care providers, administrators, patients, payers, and carriers. Although beneficial in some respects, the administrative system has increased the overall cost of health care while, at the same time, making it difficult for health care providers to receive advance payment for services rendered.

There are several reasons to account for the detrimental effect that large administrative systems have had on the advance payment of claims for health care services. For example, a single health management organization may review tens of thousands of payment requests each day and tens of millions of requests a year. The sheer volume of payment requests alone creates a backlog of unpaid claims. Additionally, the contractual obligations between parties are complex and may change frequently. Often, there are many different contractual arrangements between patients, payers or carriers, and health care providers. The amount that is authorized for payment may vary by the service or procedure, by the particular contractual arrangement with each health care provider, by the contractual arrangements between the carrier or payer and the patient regarding the allocation of payment for treatment, and by what is considered consistent with current medical practice. As a result of any changes in these contractual relationships, it is often necessary to spend additional time reviewing and analyzing claims, further delaying the payment for services rendered. This is particularly true when claims are submitted with clerical errors, in which case the claim will be disputed and may ultimately have to be resubmitted.

When a claim is disputed, it must be adjudicated to determine exactly which services are authorized and how much a health care provider will be paid. Adjudicating a claim can take several weeks or months and may require multiple submissions of the same claim. While a claim is being adjudicated, a health care provider is left without funds for services that have already been rendered, and as a result, the health care provider may suffer serious financial problems that are associated with cash flow realities.

During recent years, there has been an attempt to expedite the payment of health care services by automating the process for creating, reviewing, and adjudicating payment requests. For example, there currently exist claims processing systems whereby technicians at health care providers' offices electronically create and submit medical insurance claims to a central processing system. The technicians input information identifying the physician, patient, medical service, carrier or payer, and other data with the medical insurance claim. The central processing system verifies that the physician, patient, and carrier or payer are participants in the claims processing systems. If so, the central processing system converts the medical insurance claim into the appropriate format of the specified carrier or payer, and the claim is then forwarded to the carrier or payer. Upon adjudication and approval of the insurance claims, the carrier or payer initiates a check to the provider. In effect, such systems bypass the use of the mail for delivery of insurance claims and save overall time.

However, even using these automated systems, medical technicians at the health care provider's office are often unable to determine whether the claim, as it is submitted, is in condition for payment. If the claim is not in condition for payment then the claim will undergo a protracted adjudication, which may include multiple resubmissions of the same claim. For example, it has been found that a large number of insurance claims are submitted with information that is incomplete, incorrect, or that describes diagnoses and treatments that are not eligible for payment. Accordingly, these claims may be rejected for any of a large number of informalities, including clerical errors, patient ineligibility, indicia of fraud, etc. The health care provider, however, is not made aware of the deficiencies of the submitted claims until a later date, potentially weeks afterwards, when the disposition of the insurance claim is communicated to the health care provider. As a result, many claims are subject to multiple submission and adjudication cycles, as they are successively created, rejected, and amended. Each cycle may take several weeks or more. The resulting duplication of effort decreases the efficiency of the health care system and increases the time it takes to process a claim.

Studies have shown that some insurance claim submission systems reject up to 70% of claims on their first submission for including inaccurate or incorrect information or for other reasons. Many of the claims are eventually paid, but only after they have been revised in response to an initial rejection. Thus, while systems that permit electronic submission of insurance claims marginally decrease the time needed to receive payment by eliminating one or more days otherwise required to deliver claims by mail, they remain subject to many of the problems associated with conventional claims submission systems. Accordingly, even automated systems that are designed to improve the efficiency of the health management systems have ultimately failed to provide an adequate means for promptly paying health care providers for services rendered.

Some health care providers cannot afford the luxury of waiting an extended period of time for claims to be processed because of financial obligations related to operating expenses and overhead. This is particularly true for health care providers who purchase new equipment and hire experienced staff. Any delay in receiving payment can create cash flow problems. Accordingly, in order to attempt to minimize the number of claims that are rejected and effectively reduce the overall amount of time it will take to get paid, physicians or their staff have had to spend inordinate amounts of time investigating which treatments will be covered by various insurance carriers and insurance plans. Normally, such activity involves calling insurance carriers over the telephone. The time spent in such activities, however, increases overhead costs and represents further efficiency losses in the health care system. One consequence of the inefficient and lengthy claims processing system is that some health care providers are deterred from purchasing new equipment and hiring experienced, high-salary, staff because of cash flow constraints.

One way to improve cash flow is to require payment for services at the time of service. This, however, may be prohibitive, depending upon the cost of the health care services provided and the ability of a patient to pay. Moreover, many patients are not willing to pay for health care services at the time they are rendered because they are either covered by insurance or they believe they are covered by insurance. Depending on a patient's insurance plan and the diagnosis and treatment rendered, however, the patient may be required to make a co-payment representing, for example, a certain percentage of the medical bill or a fixed dollar amount. Because of the large number of insurance carriers and insurance plans, however, the amount of the co-payment can vary from patient to patient and from visit to visit. In fact, some insurance plans do not require the patient to make a co-payment at all, in which case the health care provider must wait for the insurance claim to be processed and adjudicated. Accordingly, the various insurance plans make it difficult to know exactly how much co-payment each patient is required to make. This is particularly true when coverage of an insurance plan is based on percentages of total services and not on flat co-payment amounts. The uncertainty regarding co-payments makes it even more difficult for health care providers to receive advance payment for services rendered, particularly for the patient's portion of costs pertaining to the health care services. Furthermore, once the patient leaves the office, the expense of collecting amounts owed by the patient increases and the likelihood of getting paid decreases.

In view of the foregoing, there is a need in the art for providing health care providers with advance payment for services rendered. For example, it would be an advancement in the art to provide a claims payment system that would enable health care providers to receive payment for services rendered prior to the completion of a conventional claims adjudication process, particularly when the adjudication process is protracted due to claim informalities and administrative inefficiencies. It would also be an advancement in the art to provide a claims payment system that would enable health care providers to know exactly how much co-payment to request from a patient prior to discharging the patient.

SUMMARY AND OBJECTS OF THE INVENTION

The present invention relates to methods and systems for promptly approving and paying health care providers for services rendered. According to the present invention, a medical technician can prepare an insurance claim electronically, submit the claim via the Internet or another wide area network, and receive almost immediately an indication whether the patient is covered by insurance and whether the submitted claim is in condition for advance payment. If the claim is not in condition for advance payment, the health care provider is notified of the claim rejection and can properly amend the claim by correcting the errors. Once it is determined that the claim is in condition for advance payment, the claim is submitted to the patient's carrier or payer for conventional claims processing and, if necessary, adjudication. The claim is simultaneously submitted to a payment entity where it is determined what finds should be advanced to the health care provider and how the funds are to be distributed.

The present invention can significantly reduce the amount of time it takes for a health care provider to receive payment for services rendered. This is particularly true when a claim is ultimately subjected to a lengthy adjudication process in the conventional claims processing by a patient's carrier or payer. The invention can also significantly reduce the time, effort, and expense that have been associated with the submission of claims that are not in condition to be paid, such as claims that are submitted with clerical errors. A medical technician can also receive an almost immediate indication of any co-payment that is required of a patient. This further enhances the likelihood and ability of a health care provider to receive advance payment for services rendered.

According to the present invention, communication is established between a client computer, operated by a health care provider, and a remote server computer. The communication can be established using the Internet, a direct-dial telephone line, or any other suitable wide area network infrastructure. The client computer displays a computer-displayable claim form to the health care provider which is used to create an insurance claim. The claim, including patient identification, insurance information, and treatment information is transmitted electronically from the client computer to the server computer. Although the present invention is most efficient when electronic claim forms are used, paper claim forms and conventional mail systems can also be used to submit claims to the remote server. The present invention is an improvement over the prior art, even when conventional mail systems are used, because it reduces the total time it takes for health care providers to receive payment for services rendered. In particular, the present invention provides systems and methods for promptly paying health care providers for services rendered, even before the claims are processed by the health insurance carrier. If paper claim forms are submitted by a participating health care provider, the claims are subsequently converted into an electronic format via OCI/OCR imaging or manual entry.

Upon receiving a claim, the remote server determines whether the claim in condition for advance payment using various auto automated processes. If necessary, the medical technician using the client computer can revise the claim to cause it to be in condition to be paid. When the remote server finally determines that the claim is in condition for advance payment, the remote server submits the claim to the patient's health insurance carrier for conventional claims processing and, if necessary, adjudication. The claim is sent electronically if the carrier is equipped to receive electronic claims. Otherwise, claims are sent by conventional mail in paper format. The claims processing and adjudication of a carrier may take several weeks or months. To expedite the payment of claims to health care providers, the present invention provides a method and a system for providing health care providers with advanced payment for services rendered, even before insurance claims for those services can be processed and adjudicated by a corresponding carrier or payer. To do this, the remote server also submits claims to a payment entity where it is determined what funds should be advanced to the health care provider and how the funds are to be distributed The remote server then transmits information to the client computer to notify the health care provider of the various determinations that have been made. The information transmitted to the client computer can include data that represents an amount that is to be paid by the carrier or payer on behalf of the patient and any co-payment to be collected from the patient. The information can also indicate how much money will be advanced to the provider to promptly pay for rendered services. Typically, this amount corresponds with the amount that is to be paid by the carrier or payer. Because these processes, as described above, can occur almost instantaneously, typically in a matter of seconds or minutes, any co-payment can be collected from the patient before the patient is discharged from the offices of the health care provider. The remaining funds can then be received either by the carrier or payer through normal operations or they can be made almost immediately available using a short-term loan.

Upon receiving claim data, the payment entity cooperates with a financial entity to advance a credit of funds into two separate accounts, an operations account and a reserve account. Explanation of payments (EOP) data can be made available for the health care provider to view over the Internet as soon as the payment entity authorizes fund distribution. The EOP data explains the distribution of funds to each of the accounts and can be updated by the payment entity and/or by the financial entity.

In one example, the operations account is credited with approximately 80% of the advance and is immediately accessible by the health care provider to meet financial obligations and to avoid cash flow problems. The reserve account is credited with approximately 20% of the advance. The funds of the reserve account are not immediately accessible to the health care provider. The reserve account is debited to cover processing fees, interest on the outstanding balance of the credit advance, and to pay down the outstanding balance of the credit advance, if any.

When the carrier or payer finally completes the processing and adjudication of the claim, the payment for services rendered is submitted to the provider's reserve account to pay down the outstanding balance and the interest on the outstanding balance. The payment to the reserve account can be made electronically with an electronic fund transfer or by check. The carrier or payer submits an explanation of benefits (EOB) form to the patient when the processing of the claim is complete. EOB data can also be made accessible online.

In view of the foregoing, the invention provides systems and methods for enabling health care providers to be promptly paid for services rendered. A claim can be submitted, verified and approved for advance payment almost instantaneously. A claim that is not in condition for advance payment can be immediately amended for approval. A health care provider is notified of the amount that is authorized for advance payment and of any co-payments that are due from the patient so that they can be collected before the patient is discharged. The approved amount of advance payment is distributed between into two accounts, one of which provides the health care provider with immediate access to funds for health care services rendered, even before the carrier or payer has paid for the services.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

The present invention relates to systems and methods for promptly paying health care providers for services rendered, even before payment requests for the rendered services can be processed and adjudicated by corresponding carrier or payers.

A medical technician at the offices of a health care provider operates a client computer that communicates with a remote server. According to one embodiment of the invention, the medical technician views a computer-displayable claim form displayed by the client computer and enters patient information, insurance plan information, and treatment information which includes a diagnosis code and a treatment code that describe a medical diagnosis and associated treatment performed on a patient by the health care provider. The patient information, insurance plan information and treatment information are transmitted to the remote server Upon receiving this information, the remote server performs an operation to determine whether the patient is approved by the carrier or payer of the insurance plan or of another insurance plan. The remote server may also perform an operation to the treatment information to determine whether the diagnosis code and the treatment code correspond to health care services that are approved for advance payment.

If the remote server determines that the patient is not covered by an approved insurance plan or that the submitted claim is not in allowable condition for advance payment, the remote server transmits information to the client computer to inform the medical technician of this result. In response, the medical technician can amend the patient information, insurance plan information or treatment information to place the claim in allowable condition for advance payment. After amending the claim, the claim is again submitted to the remote server, where it is again analyzed to determine whether the patient is covered by an approved insurance plan and whether the claim is in allowable condition for advance payment. The remote system can also inform the health care provider of any co-payment to be collected from the patient before the patient is discharged so that the co-payment can be received immediately.

According to one presently preferred embodiment, when the remote server determines that a submitted claim is in condition for advance payment, the remote server transmits the claim data to the carrier or payer for processing while simultaneously submitting the claim data to a payment entity which determines exactly how much money will be advanced for the services performed and how the funds are to be distributed. Once this determination is made, the client computer can access data over the Internet that provides an explanation of payment (EOP) regarding how much money is to be advanced and how the money is to be distributed.

In one embodiment, the approved distribution funds are distributed between two accounts of a financial entity, such as a bank. The two accounts include a reserve account and an operational account. The funds of the operational account comprise a significant percentage of the advanced funds and are immediately accessible to the health care provider. These funds are made available to the health care provider within hours or days, well before the corresponding insurance claim can be processed and adjudicated by the carrier or payer, which can take weeks or months. The reserve account is credited with the balance of the advanced funds. The funds of the reserve account are not accessible to the health care provider, but are instead debited for service fees, interest for outstanding balances, and to pay off any outstanding balances. When the insurance claim is finally processed by the carrier or payer, the claim payment is credited to the reserve account and the EOP data is updated. After expenses have been paid by the reserve account, the remaining balance is transferred to the operational account, thereby making the remaining funds available to the health care provider.

Embodiments of the invention include or are incorporated in computer-readable media having computer-executable instructions or data structures stored thereon. Examples of computer-readable media include RAM, ROM, EEPROM, CD-ROM or other optical disk storage, magnetic disk storage or other magnetic storage devices, or any other medium capable of storing instructions or data structures and capable of being accessed by a general purpose or special purpose computer. Computer-readable media also encompasses combinations of the foregoing structures. Computer-executable instructions comprise, for example, instructions and data that cause a general purpose computer, special purpose computer, or special purpose processing device to execute a certain function or group of functions. The computer-executable instructions and associated data structures represent an example of program code means for executing the steps of the invention disclosed herein.

The invention further extends to computer systems for interactively preparing and paying insurance claims and determining whether the claims are in condition to be paid. Those skilled in the art will understand that the invention may be practiced in computing environments with many types of computer system configurations, including personal computers, multi-processor systems, network PCs, minicomputers, mainframe computers, and the like. The invention will be described herein in reference to a distributed computing environment, such as the Internet, where tasks are performed by remote processing devices that are linked through a communications network In the distributed computing environment, computer-executable instructions and program modules for performing the features of the invention may be located in both local and remote memory storage devices.

1. Network Environment

Figure 1:
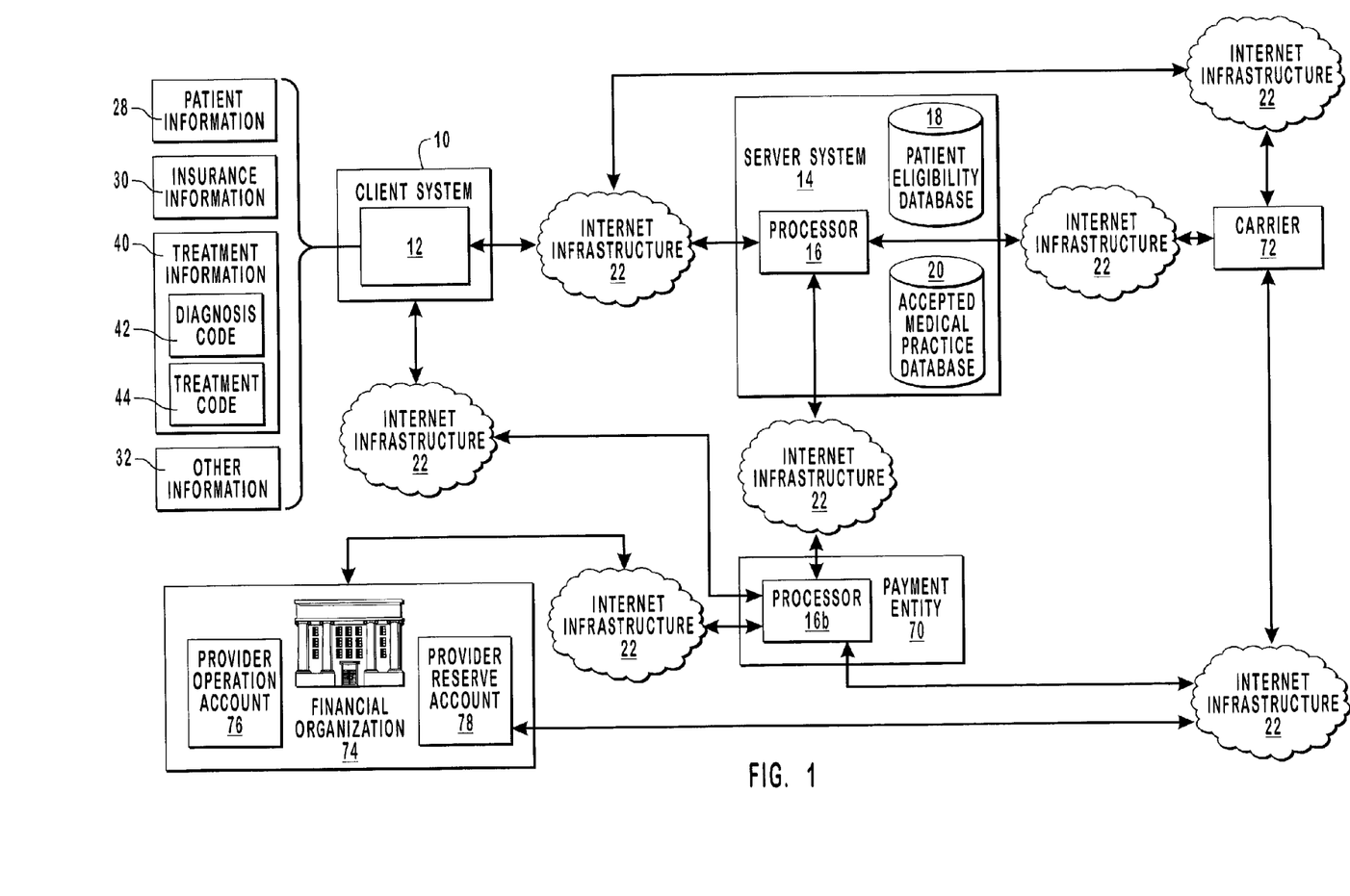
FIG. 1 is schematic diagram illustrating an interactive system according to the invention, including a client system located at the offices of a health care provider, a remote server system, a carrier or payer, a payment entity, and a financial institution that includes a reserve account and an operational account.

FIG. 1 illustrates an embodiment of the systems and methods for preparing and promptly paying health insurance claims according to the present invention. Client system 10 may be located at the offices of a health care provider in order to allow a medical technician to create and submit insurance claims. As used herein, the term "health care provider" is to be broadly construed to include any physician, dentist, medical practitioner, or any other person whose services can be compensated by a health insurance carrier or payer, a health maintenance organization, or the like. As used herein, the term "medical technician" represents any person who engages in the activity of preparing or submitting insurance claims on behalf of a health care provider. Since medical technicians are typically employees of health care providers, representatives of health care providers, or may be the health care providers themselves, any of the claims that recite acts, operations, or processes conducted by "health care providers" are to be construed to extend to the same acts, operations, or processes conducted by "medical technicians", as well. The terms "carrier" and "payer" are generally interchangeable, and any reference to "carrier" in the specification or claims extends to entities that can be classified as "payers" unless otherwise specified.

The term "insurance plan" extends to any contractual or other legal arrangement whereby medical and other related expenses are paid by a carrier on behalf of a patient beneficiary. Examples of insurance plans include health maintenance organizations, fee-for-service health care plans, employer-sponsored insurance plans, etc.

Client system 10 can be a general purpose computer, such as a personal computer, or a special purpose computer adapted to perform the functions and operations disclosed herein. Client system 10 may include a display device such as a monitor for displaying claim form 12, as will be disclosed in greater detail below, and one or more input devices such as a keyboard, a mouse, etc. for enabling a medical technician to enter the required information to client system 10.

The embodiment illustrated in FIG. 1 also includes a server system 14 located typically at a remote location with respect to client system 10. Server system 14 can include a general purpose computer or a special purpose computer adapted to execute functions and operations of the invention. For example, in FIG. 1, server system 14 includes a processor 16, which represents a general purpose computing device for receiving information associated with insurance claims and for determining whether the received insurance claim is in allowable condition for advance payment. The operation of server system 14 and processor 16 will be discussed in greater detail below.

In one embodiment, processor 16 is capable of accessing information stored in a patient eligibility database 18 and an accepted medical practice database 20. Database 18 can include compilation of data that enables server system 14 to determine whether a particular patient identified at client system 10 is a beneficiary of an approved insurance health plan. Likewise, database 20 can be any compilation of data that enables service system 14 to determine whether the health care services associated with a submitted claim are approved for advance payment. Generally, a submitted claim is approved for advance payment if it is determined that the patient is a beneficiary of an approved insurance carrier/plan and the services rendered are qualified services under the particular insurance plan of the patient.

While the illustrated components of server system 14 of FIG. 1 can be located at a single remote site with respect to client system 10, other embodiments of the invention employ a processor 16 and databases 18 and 20 that may be located at different sites with respect to each other. The terms "server system" and "remote server" extend to the latter case, wherein the various components 16, 18, and 20 are located in a distributed environment unless specifically indicated otherwise.

In the embodiment of FIG. 1, client system 10 and server system 14 communicate by means of Internet infrastructure 22. While the invention is described herein in the context of the Internet, those skilled in the art will appreciate that other communications systems can be used, such as direct dial communication over public or private telephone lines, a dedicated wide area network, or the like. It should also be appreciated that the present invention, although preferably practiced over an Internet infrastructure, can also be practiced using conventional paper mailing systems and paper claim formats. However, before the server system can determine whether a claim is in allowable condition for advance payment, the claim must first be converted into an electronic format. This can be accomplished by using any suitable optical character recognition (OCR) or optical character imaging (OCI) software and hardware, or by manual data entry.

2. Claim Preparation and Adjudication

The following discussion relates to processes of creating and adjudicating insurance claims using a computer network. Although the following techniques can facilitate the insurance claim creation and adjudication process, the methods of paying insurance claims according to the invention, including advancing funds to the health care provider using a short-term loan, can be practiced in connection with insurances claim prepared and adjudicated in other ways, such as other electronic or paper insurance claims. Further details relating to the following insurance creation and adjudication processes are disclosed in U.S. patent application Ser. No. 09/118,668, filed Jul. 17, 1998, entitled "Internet Claims Processing System," and U.S. patent application Ser. No. 09/204,886, filed Dec. 3, 1998, entitled "Provider Claim Editing and Settlement System," both of which are incorporated herein by reference.

Referring to FIG. 1, when a medical technician desires to prepare an insurance claim for health care services, the medical technician operates client system 10 and establishes communication with server system 14 or verifies that communication has been established. For instance, the medical technician may use client system 10 to dial into a modem pool associated with an Internet service provider in Internet infrastructure 22. After communication with the Internet service provider has been achieved, client system 10 may be used to transmit a Uniform Resource Locator (URL) to the Internet infrastructure 22 that requests access to resources provided by server system 14. Alternatively, any other suitable technique can be used to establish communication between client system 10 and server system 14.

In many cases, client system 10 can maintain communication with server system 14 for an extended period of time during which claims for multiple patients are processed. For instance, client system 10 can be a dedicated terminal that maintains communication with server system 14 in order for numerous insurance claims to be created and processed.

Once communication has been established, the medical technician can use client system 10 to request claim form 12 to be displayed on a monitor associated with client system 10. Claim form 12, in one embodiment, is a Hyper Text Markup Language (HTML) document retrieved from server system 14 and displayed to the medical technician. Alternatively, claim form 12 can have any other suitable format or can be stored at a local cache or any other local data storage system, thereby eliminating the need to repeatedly retrieve claim form 12 from a remote location as multiple insurance claims are created.

Figure 2:
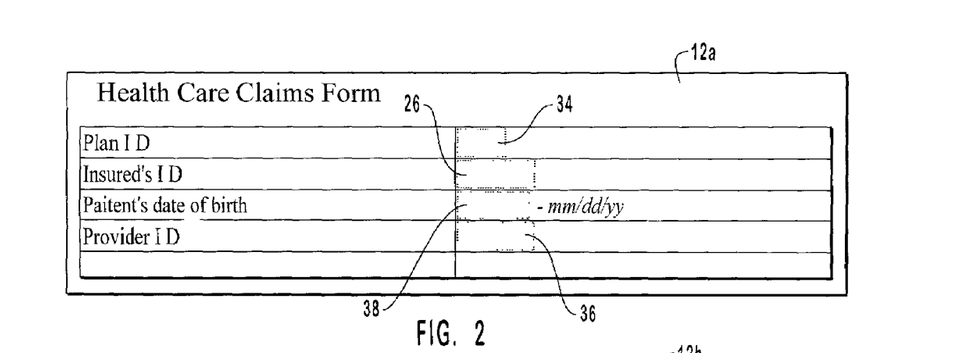
FIG. 2 illustrates an insurance claim form that enables a medical technician to determine whether and to what extent a patient is a beneficiary of an approved insurance plan.

FIG. 2 illustrates one example of a claim form 12A that enables a medical technician to verify that a patient is a beneficiary of an insurance plan and to learn of the details of the insurance plan. In this embodiment, claim form 12A includes a field 26 to which a patient identifier can be entered. Patient identification information, such as patient information 28 of FIG. 1, is entered by the medical technician into claim form 12A of FIG. 2. Depending on the manner in which the invention is implemented, the medical technician may be required to enter other information, such as insurance information 30 of the patient, or other information 32 of FIG. 1. Other information 32 may include health care provider identification, or the like. Returning to FIG. 2, claim form 12A includes a field 34 for identifying the insurance plan of the patient, a field 36 for receiving information identifying the health care provider and a field 38 for entering additional information identifying the patient. As shown in FIG. 2, field 38 can be adapted to receive a patient's date of birth. Alternatively, any other information that can uniquely identify a particular patient from among a pool of patients can be used in combination with fields 26 and 38. By way of example and not limitation, the patient identification information entered to fields 26 or 38 can be modified to include patient's social security number, or any other number uniquely associated with the patient by a carrier or a health maintenance organization.

Referring now to FIG. 1, after the medical technician has entered patient identifier 28, insurance information 30, and, optionally, other information 32, the medical technician uses client system 10 to transmit the information to server system 14. In one embodiment, processor 16 compares patient identifier 28 against data stored in patient eligibility database 18 to determine if the patient is a beneficiary of an insurance health plan and, if so, the details of the benefits thereof. If the patient is found not to be a beneficiary of an approved insurance health plan, information is transmitted from server system 14 to client system 10 to inform the medical technician of this result. Thus, when the patient is not a beneficiary, a medical technician and the health care provider can promptly learn of this status and take appropriate steps to modify the claim to correct errors, if any, that prevented the patient from being recognized as a beneficiary of an approved health insurance plan.

If it is determined that the patient is a beneficiary, information is likewise transmitted from server system 14 to client system 10 informing the medical technician of the patient's status. This information can also provide details of the coverage provided to the patient that can allow the health care provider to know how much of a co-pay to request from the patient before the patient is discharged from the office. Information can also contain details regarding the types of diagnoses and treatments that are approved for payment, as well as corresponding diagnosis and treatment codes, so that the medical technician does not have to spend inordinate amounts of time researching to know what codes correspond to the services performed.

Figure 3:
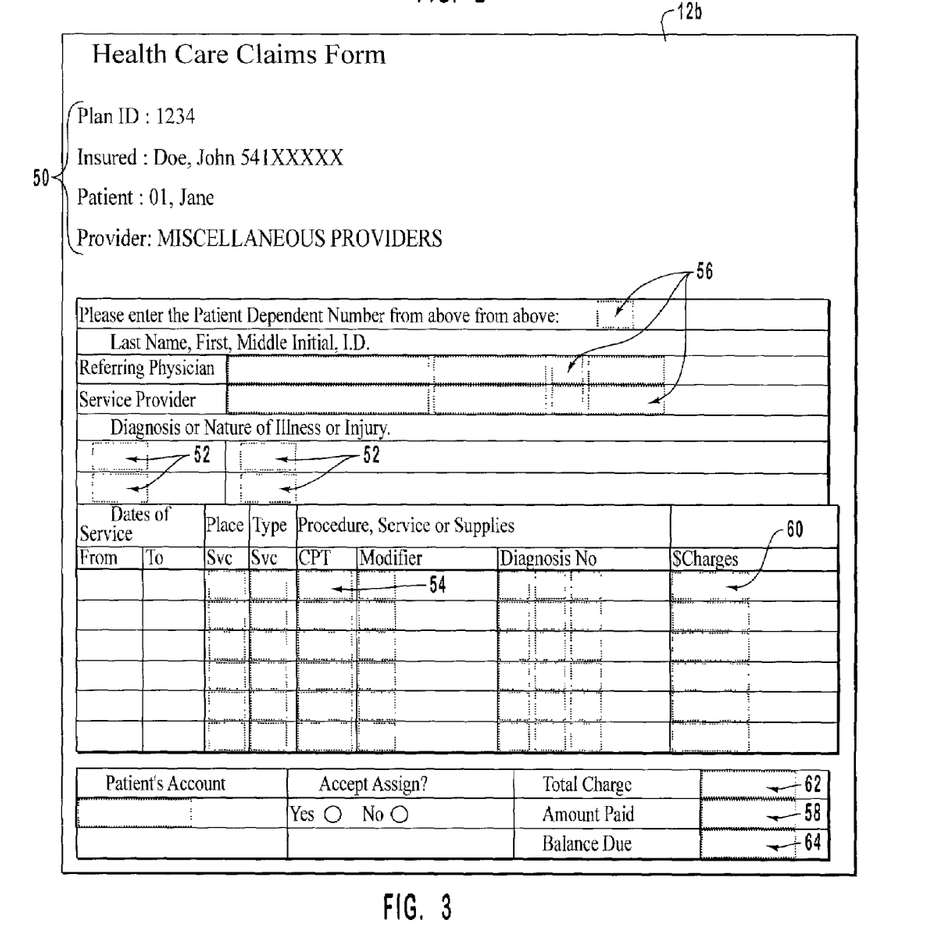
FIG. 3 illustrates an insurance claim form that enables a medical technician to submit an insurance claim including one or more diagnosis codes and one or more treatment codes.

The medical technician can complete the claim form by entering treatment information 40 that includes at least one diagnosis code 42 and one treatment code 44. Referring now to FIG. 3, claim form 12B includes fields specifically adapted to accept the diagnosis code 42 and the treatment code 44. Claim form 12B of FIG. 3 and claims form 12A may be separate forms displayed to the medical technician using client system 10 or can be separate portions of the single claim form. Claim form 12B, in the example of FIG. 3, includes header information 50 that has been automatically prepared by the server system before claim form 12B was transmitted to the client system. Providing a claim form 12B that is automatically partially completed contributes to the efficiency of the claims creation and submission processes of the invention. While claim form 12B represents a claim form that can be advantageously used by many health care providers, the specific fields included the form and the information displayed on the form may vary from one implementation to another, depending on the type of health care provider, insurance plan, and other factors.

Claim form 12B includes a plurality of fields 52 designed to receive and display diagnosis codes representing the health care provider's diagnosis of the patient or the nature of the patient's illness or injury. Thus, as used herein, "diagnosis code" refers to any information that specifies or indicates a patient's condition as diagnosed by a health care provider. Any predefined set of diagnosis codes can be used with the invention.

Claim form 12B also includes one or more fields 54 designed to receive and display treatment codes associated with the diagnosis code of field 52. As used herein, "treatment codes" can represent any type of health care services, including, but not limited to clinical therapy, pharmacological therapy, therapeutic supplies or devices, and other goods or services that can be paid for by health insurance plans or health maintenance organizations. The treatment codes can be selected from any desired set of predefined treatment codes that define various treatments that can be administered to patients. In one embodiment, the diagnosis codes and the treatment codes can be selected from the codes and code modifiers of a volume entitled Physician's Current Procedural Terminology (CPT), which is maintained and updated annually by the American Medical Association.

As shown in FIG. 3, claims form 12B can also include other fields, such as fields 56, that are to be completed by the medical technician before the insurance claim is submitted. In this example, fields 56 are adapted to receive and display information identifying the patient, a referring physician, and the health care provider who is to receive payment for the rendered health care services.

When fields 52, 54, and 56 are filled out by the medical technician, the medical technician submits the information included in these fields to server system 14 from client system 10. Referring again to FIG. 1, server system 14 receives this information and performs a claim verification process, in response thereto, to determine whether the claim, as submitted, is in condition for advance payment for services rendered. Typically, a determination that the claim is in condition for advance payment is made if the claimed services correspond to health care services that are approved for payment by the patient's insurance plan. For instance, processor 16 can compare the diagnosis code 42 and treatment code 44 with a compilation of currently accepted medical procedures stored in database 20. In one embodiment, a database of prevailing health care charges, such as the Medical Data Research (MDR) database, or a customized database compiled by an entity operating the payment system of the invention is used to determine whether the diagnosis codes and treatment codes correspond to health care services that are approved for payment. Upon learning of the invention disclosed herein, those skilled in the art will understand how an MDR database or another database can be used to determine whether the submitted claim form represents health care services that are approved for payment.

Database 20 can alternatively be one that is compiled or supplemented on an ongoing or repeated basis as the entity that authorizes the insurance claims for advance payment processes large numbers of insurance claims associated with particular payers or insurance carriers. For example, the processes disclosed in U.S. patent application Ser. No. 09/634,679, filed Aug. 8, 2000, entitled "Determining the Degree of Acceptance of Proposed Medical Treatment," which is incorporated herein by reference, can be adapted for this purpose.

Server system 10 also determines whether the information provided in claim form 12B is sufficiently complete to place insurance claim in condition to be paid. For example, if the medical technician inadvertently fails to include information that identifies the physician, server system can detect this error and notify client system 10 of the deficiency so that it can be remedied.

The claim verification process that is performed by server system 14 can be as complex as desired. In one embodiment, server system 14 analyzes the information submitted using claim form 12B to determine whether there are indicia of fraud or mistake, whether unusually expensive health care services are listed in the claim, or whether other anomalies are present that suggest the claim is not suitable for advance payment according to the present invention.

One technique that is sometimes used by health care providers to collect more money from insurance plans than is otherwise warranted is the practice of unbundling medical procedures. "Unbundling" consists of performing, for example, multiple medical procedures on a patient through a single surgical incision while submitting an insurance claim for the multiple medical procedures as if they had been performed separately. Typically, when only one incision is required to perform multiple medical procedures, the payment to the operating physician is less than the payment would be if each of the multiple medical procedures had been conducted through separate incisions. Other fraudulent unbundling techniques for submitting claims on multiple medical procedures are sometimes used as well. Thus, server system 14 can analyze the diagnosis codes and the treatment codes for indicia of unbundling practices. Furthermore, server system 14 may conduct any other checks on the submitted claim. For example, the server system 14 may cross reference the patient gender with the diagnosis and treatment codes. In would be inappropriate, for example, for a hysterectomy to be performed on a male or a vasectomy to be performed on a female.

If the claim exhibits any of the foregoing features, the claim may be denied eligibility for advance payment of funds for services rendered. In which case, the health care provider will have to wait until the claim is processed and adjudicated by a corresponding carrier. Alternatively, the claim may be returned to the health care provider to allow revision of the claim. For example, the server system 14 can transmit reply information to client system 10 informing the medical technician of a negative result and can indicate the basis for rejecting a claim. Thus the medical technician can be informed that the claim form was not completely filled out, the treatment code is inconsistent with the diagnosis code, or any of a number of other possible reasons for rejecting the insurance claim. In response, the medical technician can amend the insurance claim by entering the correct information to the fields of claim form 12B of FIG. 3, if necessary. In other cases, the health care provider can be informed of what diagnosis and treatment codes are appropriate for the services that were performed and will be approved for advance payment, according to the patient's insurance plan.

If the medical technician wishes to amend the insurance claim, the new information is transmitted from client system 10 to server system 14 for processing. Server system 14 then repeats the previously described claim verification process of determining whether the amended insurance claim is in allowable condition for advance payment. The above-described procedure can be repeated as many times as desired or necessary to create and submit an insurance claim that describes health care services that are approved for payment by the patient's insurance plan, and subsequently eligible for advance payment prior to the carrier actually processing the claim. It should be appreciated that even if it is ultimately decide that a submitted claim is not eligible for advance payment, the claim verification process of the present invention, which can take just minutes even when resubmissions are required, significantly reduces the time it takes for a claim to be processed and, if necessary, adjudicated by a carrier. This is particularly true when the claim verification process identifies clerical errors that can be identified and corrected almost instantaneously. It should be appreciated that this is an improvement over the prior art for at least informing a health care provider of correctable claim errors early on so that a health care provider does not have to engage in extensive research, telephone conversations or hold time, and mail adjudications just to place a claim in allowable condition to be paid.

Even though the processing and adjudication of insurance claims may be expedited in some degree by the foregoing description of the present invention, some health care providers find that processing of insurance claims by corresponding carriers still takes too long for their needs. This is true even when the claims are submitted in allowable condition for payment and are paid as expeditiously as possible through the carrier administrative systems. To remedy this problem, the present invention provides a method and system of promptly paying health care providers for services rendered, even before the corresponding insurance claims can be processed by the appropriate carrier. In particular, the present invention provides a payment entity 70, as shown in FIG. 1, which advances a credit of funds to the health care provider for rendered services.

3. Payment of Insurance Claims by Advancing Funds

Returning to FIG. 1, once the server system 14 determines that a claim is eligible for advance payment, the server system 14 transmits claim data to a payment entity 70, which is in communication with the server system 14 through the Internet infrastructure 22. It should be appreciated that the payment entity 70 includes at least one server computer to perform the functions described herein by using appropriate computer-readable media and computer-executable instructions. In one embodiment, the payment entity 70 uses a processor 16b to pre-adjudicate the submitted claim. In an alternative embodiment, the payment entity 70 used the processor 16 of the server computer to pre-adjudicate the submitted claim. Pre-adjudication involves determining how much money will be advanced for the claimed services. This determination is made by comparing any combination of the patient information 28, insurance information 30, treatment information 40, and other information 32 with archived records of insurance payment histories, similar claim payment results, adjudication rules, and the like. Pre-adjudication also may involve determining how the funds, if approved, are to be distributed and into which accounts they are to be distributed.

In one embodiment, the payment entity 70 communicates the resulting data of the pre-adjudication to server system 14. The resulting data includes financial information which the server system 14 subsequently transmits to client system 10 to inform the health care provider that the submitted claim is in condition for advance payment and the amount that will be advanced for services rendered. As a matter of example, claim form 12B of FIG. 3 may include in the amount paid field 58 a dollar amount that is to be promptly paid for services rendered. The advance may be equal to the amount that was previously determined as being likely to be paid by the carrier on behalf of the patient. Receiving this information permits the medical technician to know exactly how much money to request from the patient for services rendered, in the form of a co-payment.

To illustrate, the medical technician might enter in field 54 a treatment code that represents a physical exam performed by a physician. The medical technician could then enter in field 60 a dollar amount, such as $100, that represents the physician's charges for performing the physical exam. Field 62 sums all dollar amounts entered in fields 60. In this example, if the physical exam was the only treatment rendered to the patient, field 62 would also display a dollar amount of $100. If, however, the payment entity 70, when pre-adjudicating the submitted claim, determines that the patient's carrier typically pays only $90 for a physical exam, field 50 displays the dollar amount of $90 that is eligible for advanced payment according to the invention. A balance due field 64 displays the difference between the total charge field 62 and the amount paid field 58. Accordingly, the dollar amount displayed in field 64 represents the amount that should be collected from the patient for services rendered. As used herein, the term "co-payment" is defined to extend to the dollar amount displayed in field 64, representing the amount that is to be collected from the patient beyond the payment that is approved for payment by the carrier.

In another embodiment, the amount paid field 58 does not represent the amount that will be advanced in the form of an advance payment, but rather, it represents the coverage amount of the patient's insurance plan. According to this embodiment, the health care provider can access EOP data, if desired, on the Internet infrastructure by accessing an EOP website that is updated by the payment entity and/or by corresponding financial entities.

Although the previous example goes into some detail regarding how the payment entity 70 and the server system 14 are in communication, suggesting they are discrete entities, it should be appreciated that the payment entity 70 and the server system 14 can comprise a single organization or single server system.

Using the present invention, medical technicians and health care providers can be informed of the status of submitted insurance claims in a relatively short amount of time that is significantly less than conventional systems, which may require days, weeks, or more. Indeed, for practical purposes, a response to the submitted insurance claim is received almost immediately by the medical technician. It can be understood that the limiting factors with respect to the speed of response include the data transmission rate supported by Internet infrastructure 22 of FIG. 1 and the other communication links between the various components of the system, the processing capabilities of processor 16 and other components of server system 14, and the complexity of the submitted claim and the nature of the claim processing techniques performed by server system 14. Accordingly, although it was previously mentioned that paper claims can be submitted and subsequently converted to electronic form, payment generally occurs earlier when communication between the client system 10, server system 14, and payment entity occurs via an electronic medium, such as the Internet infrastructure 22.

When an electronic medium is used, the response time is short enough that a medical technician can conveniently continue viewing the claim form associated with a particular patient at client system 10 while server system 14 performs the operations that determine whether the submitted claim is in condition to be paid and while the payment entity 70 pre-adjudicates the claim to determine what finds if any will be made available for advance payment. Thus, a medical technician can efficiently and consecutively create and submit a series of claims and receive verification that the claims are in allowable condition for advance payment. In other words, a medical technician can easily create, submit, and, if necessary, revise and resubmit, a single claim before proceeding to the next claim in a series of claims, since the response time can be very short. This is in sharp contrast to prior art systems in which the response time of days, weeks, or longer make it entirely impractical for medical technicians to complete the entire claim creation and adjudication process for one claim before proceeding to the next claim.

FIG. 1 also shows that the server system 14 is in communication with a carrier 72, which represents any health insurance company, health maintenance organization, fee-for-service service health care company, employer-sponsored health insurance, etc. The carrier includes appropriate computer-readable media and computer-executable instructions to perform the functions described herein. In one embodiment, server system 14 transmits claim information to the carrier 72 simultaneously with the transmission of the claim information to the payment entity 70. If the carrier 72 is not able to receive electronic claim data transmitted over the Internet infrastructure 22, then the server system produces paper claim documents that are mailed to the carrier 72 via conventional paper mail systems. The carrier 72 processes the insurance claim, which may include adjudication. However, because most of the claims that are transmitted from the server system are prescreened by the claim the verification process, it is unlikely that a claim will require extensive adjudication. It should be appreciated that this improves the overall efficiency of the carrier 72 claim processing and adjudicating processes. Despite this improvement, however, some health care providers would prefer to have more immediate payment for rendered health care services. To meet this demand, the payment entity 70 transmits a fund distribution request to a financial entity 74, such as a bank, requesting that advanced funds be credited into an account that are immediately accessible to the health care provider for rendered health care services. The financial entity 74 may include computer systems and servers to perform the functions described herein by using appropriate computer-readable media and computer-executable instructions.

According to one embodiment, the fund distribution request provides information for the financial entity 74 to know exactly how much money to advance and how to distribute the funds. The fund distribution request may, for example, request that the funds be distributed between a provider operational account 76 that is accessible to the health care provider and a provider reserve account 78 that is not accessible to the health care provider. The funds distributed to the provider operational account 76 are immediately accessible to the health care provider, whereas the funds in the provider reserve account are not accessible to the health care provider, but instead are debited for service fees, interest on any unpaid balances, and to pay off any unpaid balances.

The following is one example of how a fund distribution request may occur and how it enables a health care provider to receive advance payment for rendered health care services. As a matter of illustration only, a health provider submits a claim for $100. After being subjected to the claim verification process by the server system 14 and the pre-adjudication process by the payment entity 70, it is determined that the $100 claim is eligible for an advance payment of only $90. Within minutes or hours, the payment entity 70 submits a fund distribution request to the financial entity 74 for payment of $90 to be paid distributed between two accounts, $72 (80% of $90) into the provider operational account 76 and $18 (20% of $90) into the provider reserve account 78. Accordingly, the health care provider is then given immediate access to $72 for rendered services, even though the payment request submitted to the carrier may not be paid for weeks or months.

Finally, once a carrier 72 completes the processing of a claim and submits payment for the claim, the funds are credited to the provider reserve account 78 to pay for previously identified expenses. This transfer of funds can occur either electronically or manually. Any funds remaining in the reserve account 78 after expenses are paid are transferred to the provider operational account 76 and are accessible by the health care provider. EOP data regarding fund distribution requests and actual account transactions is updated and available through the Internet infrastructure 22. EOP data provides health care providers with immediate access to information regarding what funds are available and what credits and debits have been made to the reserve account. This information can be updated by the financial entity 74 and/or by the payment entity 70. Once a carrier 72 processes the claim, it submits explanation of benefits (EOB) data to the patient, which can be received by mail or accessed electronically of the Internet infrastructure 22.

Figure 4:
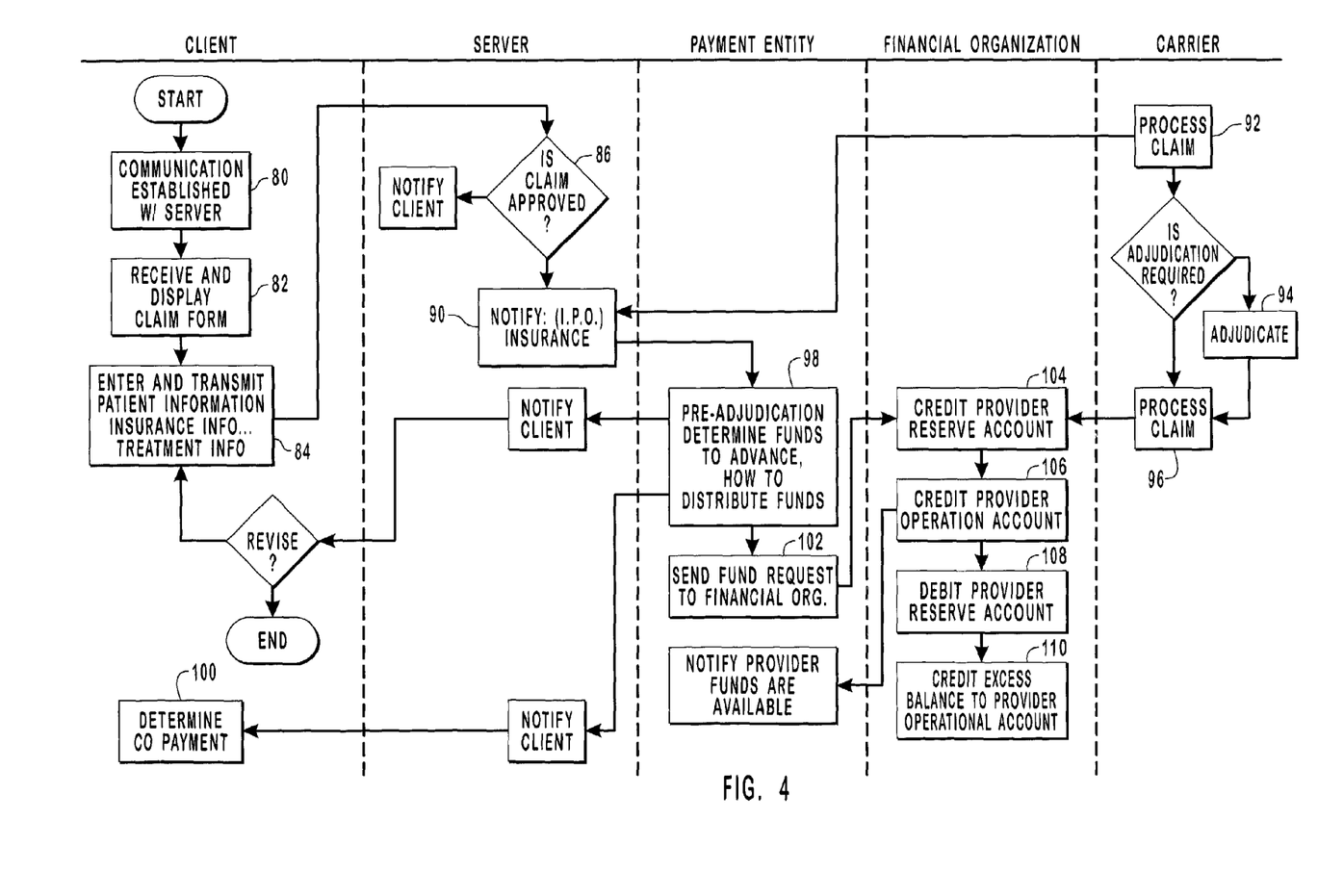
FIG. 4 is a flow diagram illustrating one embodiment of the methods of the invention for paying a claim after determining that the claim is in allowable condition for advance payment.

FIG. 4 illustrates a flow diagram of one embodiment of the present invention. As shown, in step 80, communication is established between the client system and the server system as described herein. In step 82, the client system receives and displays the claim form to enable the medical technician to enter the information required to complete the insurance claim. As previously noted, the client system can retrieve the claim form from the remote server system or from a local data storage device. In step 84, the medical technician enters the patient information, insurance information, and treatment information to the server system.

In step 86, the server system determines whether the patient is a beneficiary of an approved insurance plan. The server system, in step 86, may also subject the claim to a claim verification process to verify that the claim does not contain irregularities and to verify that the claim is eligible for advance payment. If it is determined that the claim, as submitted, is not in condition for advance payment or if the patient is not a beneficiary of an approved insurance plan then the client is notified. The claim can then be revised and resubmitted until the claim is placed in condition for advance payment, if possible.

In step 90, after determining that the claim is approved for advance payment, the server system notifies the appropriate carrier of the insurance claim. In response, as shown in step 92, the carrier begins processing the claim. If adjudication is necessary then the carrier adjudicates the claim, as shown in step 94. Finally, after processing the claim, step 92, and, if necessary, after adjudicating the claim, step 94, the carrier provides payment for the rendered health care services, step 96. The payment is made to the provider reserve account, step 92, which is debited, step 108, for services and advanced funds that were previously provided to the health care provider. As shown in step 98, the payment entity determines how much money to advance to the health care provider for services rendered and how the funds are to be distributed. The server is notified of the resulting decision, which is subsequently passed on to the client system. At that point, in step 100, the client system determines what co-payment, if any, is required from the patient.

The payment entity submits a fund distribution request to the financial entity, step 102, instructing the financial entity to advance a credit of funds between a provider reserve account, step 106, and a provider operational account, step 108. The provider reserve account is credited, step 104, with designated advance funds and with any payments that are made from carriers for processed claims. The funds in the reserve account are not immediately accessible to the health care provider, but instead are debited, step 108, to pay for any service fees, interest, and to pay down any unpaid balance. Any remaining balance in the provider reserve account is credited to the provider operational account, step 110. The funds in the provider operational account are immediately available to the health care provider.

The systems and methods disclosed herein can be practiced in combination with the systems disclosed in U.S. patent application Ser. No. 09/204,886, entitled "Provider Claim Editing and Settlement System", filed Jul. 17, 1998, which is incorporated herein by reference. For example, the claim preparation and editing systems of the foregoing patent application can be employed to determine whether health services are approved for payment prior to performing health care services. Furthermore, the methods of the present invention can be adapted according to the methods disclosed in the foregoing patent application to determine whether health services are eligible for advance payment prior to performing such services.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. In a server system capable of communicating with a payment entity, a carrier, and a client computer associated with a health care provider, a method of advancing payment for health care services rendered by the health care provider, in response to an insurance claim, and prior to the carrier making payment on the insurance claim, the method comprising the acts of:

receiving an insurance claim from a client computer, the insurance claim including patient information, insurance information, and treatment information;

determining by a server system whether the insurance claim is eligible for advance payment by determining:

whether the treatment information corresponds to health care services that are approved for payment using an accepted medical practice database, and whether the patient is an approved beneficiary of the carrier using a patient eligibility database;

transmitting, by the server system, claim information associated with the insurance claim to the payment entity, wherein, upon receiving the claim information, the payment entity advances a first portion of an advance payment to a first account accessible to the health care provider and a second portion of the advance payment to a second account prior to the carrier making payment on the insurance claim, wherein a remaining part of the second portion of the advance payment is credited to the first account after debiting the second portion for at least one of service fees, interest, or unpaid balances;

transmitting the insurance claim to the carrier;

receiving payment from the carrier at the payment entity after the carrier adjudicates the insurance claim; and distributing the payment to the payment entity to pay, wherein, upon receiving the insurance claim, the carrier makes payment on the insurance claim to the payment entity after adjudicating the insurance claim, thereby paying for the money advanced to the health care provider.

2. A method as defined in claim 1, wherein if it has been determined that the insurance claim is not eligible for advance payment, the method further comprises the acts of:

receiving from the client computer, prior to the patient being discharged by the health care provider, a revised insurance claim that includes revised treatment information; and determining whether said revised insurance claim is eligible for advance payment.

3. A method as defined in claim 1, wherein upon receiving notice from the payment entity the remote server computer further performs the act of transmitting information to the client computer that indicates how much money is approved for advance payment of the insurance claim.

4. A method as defined in claim 1, wherein the method further comprises the act of transmitting information to the client computer indicating to the health care provider whether the insurance claim is eligible for advance payment.

5. A method as defined in claim 1, wherein upon determining that the insurance claim is eligible for advance payment, the method further comprises the act of receiving a notice from the payment entity that identifies how much money will be advanced to the health care provider.

6. In a system comprising a client computer, a remote server computer, a payment entity, a carrier, and a financial entity, a method of paying a health care provider for rendered health care services before an insurance claim for the rendered health care services can be processed by the carrier, the method comprising the acts of:

receiving, at the client computer, patient information, insurance information, and treatment information entered by a health care provider to a computer-displayable claim form displayed by the client computer;

transmitting an insurance claim that includes the patient information, insurance information, and treatment information from the client computer to the remote server computer;

determining, by the remote server computer, whether the insurance claim is eligible for advance payment, wherein the insurance claim is revised at the client computer if the insurance claim is not eligible for advance payment until the remote server computer determines that the insurance claim is in condition for advance payment;

transmitting claim information from the remote server computer to the carrier and to the payment entity;

determining by the payment entity how much money should be advanced for the rendered health care services and determining how that money should be distributed;

transmitting a fund distribution request from the payment entity to the financial entity prior to the carrier adjudicating the insurance claim;

distributing, by the financial entity, credit between an operational account that is accessible to a provider and a reserve account that is not accessible to the provider;

debiting a portion of the credit in the reserve account at least for service fees; and crediting a remaining part of the portion of the credit in the reserve account to the operational account after the claim is adjudicated by the carrier.

7. A method as defined in claim 6, wherein the act of determining whether the insurance claim is eligible for advance payment comprises the act of determining whether the patient is a beneficiary of the carrier.

8. A method as defined in claim 7, wherein the act of determining whether the insurance claim is eligible for advance payment further comprises the act of determining whether the treatment information corresponds to health care services that are approved by the carrier.

9. A method as defined in claim 8, further comprising the act of transmitting, from the remote server to the client computer, a suggested revised treatment code that corresponds to the health care services rendered.

10. A method as defined in claim 6, wherein if it has been determined that the insurance claim is not in condition to be paid, transmitting a revised insurance claim that includes at least revised patient information from the client computer to the remote server computer, prior to discharging the patient who received the health care services, to determine whether said revised insurance claim is in condition to be paid.

11. A method as defined in claim 6, wherein the carrier performs the act of processing the insurance claim after the server computer performs the act of transmitting claim information to the carrier.

12. A method as defined in claim 11, wherein the act performed by the financial entity of distributing credit between the provider operational account and the provider reserve account occurs prior to the act performed by the carrier of processing the insurance claim.

13. A method as defined in claim 12, wherein upon completing the act of processing the insurance claim, the carrier further performs the act of making a payment to the financial entity to pay for the insurance claim.

14. A method as defined in claim 13, wherein the payment by the carrier is credited to the provider reserve account.

15. A method as defined in claim 6, wherein the credit distributed into the provider operational account is immediately accessible to the health care provider.

16. A method as defined in claim 15, wherein the credit distributed into the provider reserve account is not accessible by the health care provider, and wherein the reserve account is debited for service fees, interest payment, and to pay down any unpaid balance on credit made to the provider operational account and the provider reserve account.

17. A method as defined in claim 6, wherein explanation of payment data is provided over the Internet and is updated by at least one of either the payment entity and the financial entity.

18. A method as defined in claim 6, wherein the computer-displayable form is a hypertext markup language document.

19. A method as defined in claim 6, wherein if it has been determined that the insurance claim is eligible for advance payment, further performing the act of transmitting from the server computer to the client computer information that indicates an amount to be paid by the carrier to the health care provider, prior to discharging the patient from the offices of the health care provider.

20. A method as defined in claim 6, wherein if it has been determined that the insurance claim is eligible for advance payment, further performing the act of transmitting from the server computer to the client computer information that indicates how much of a co-payment is required of a patient, prior to discharging the patient from the offices of the health care provider.

21. A method as defined in claim 20, further comprising the act of collecting the co-payment from the patient based on the co-payment information.

22. In a client computer capable of communicating with a remote server computer that is in communication with a payment entity, a method of interactively preparing an insurance claim that is eligible for advance payment for health care services performed on a patient, the method comprising the acts of:

generating a computer-displayable claim form for display to a health care provider on a client computer;

receiving patient information, insurance information, and treatment information entered to the claim form by the health care provider at the client computer;

transmitting an insurance claim that includes the patient information, insurance information, and treatment information from the client computer to the remote server computer;

receiving information at the client computer from the remote server computer indicating to the health care provider that the insurance claim is not in allowable condition for advance payment, the information having been received in response to the remote server computer determining whether the treatment information corresponds to health care services that are approved for payment; and revising the insurance claim by amending at least one of a diagnosis code or a treatment code;

transmitting the revised insurance claim from the client computer to the remote server computer to determine whether said revised insurance claim is in allowable condition for advance payment;

providing said revised insurance claim to a payment entity that issues a fund distribution request to a financial entity prior to a carrier adjudicating the revised insurance claim, the fund distribution request dividing the advance payment between an operational account accessible to the health care provider and a reserve account that is not accessible to the health care provider;

debiting a portion of the advance payment in the reserve account for at least one of service fees, interest, and unpaid balances; and transferring a remaining part of the portion of the advance payment to the operational account after the carrier adjudicates the claim corresponding to the advance payment.

23. A method as defined in claim 22, wherein if the information from the remote server computer indicates that the insurance claim is in allowable condition for advance payment, the method further comprises the act of, prior to discharging the patient, the client computer receiving from the server computer information that indicates how much money the patient should pay for a co-payment.

24. A method as defined in claim 22, wherein the treatment information includes at least the diagnosis code and the treatment code.

25. A method as defined in claim 22, wherein if the information from the remote server computer indicates that the insurance claim is in allowable condition for advance payment, the method further comprises the act of displaying information that indicates how much money will be advanced to a provider account to pay for rendered health care services that are identified in the insurance claim.

26. A method as defined in claim 25, wherein the information that indicates how much money will be advanced to a provider account is displayed after it is received by the client computer from the remote server computer, and wherein the remote server computer receives the information from the payment entity.

27. A method as defined in claim 26, wherein the new information that indicates how much money will be advanced to a provider account displayed after the client computer accesses the information on the Internet, and wherein the information is generated by the payment entity.

28. A computer program product for implementing, in a server system that communicates with a client system, a payment entity and a carrier, a method of informing a health care provider who uses the client computer whether an insurance claim for health care services rendered to a patient is approved for advance payment, the computer program product comprising: a computer-readable medium carrying computer-executable instructions for implementing the method, the computer-executable instructions comprising:
 program code means for receiving an insurance claim that includes patient information, insurance information, and treatment information from the client computer, the patient information, insurance information, and treatment information having been entered to the client computer by a health care provider;
 program code means for determining whether the insurance claim is eligible for advance payment, by:
  determining whether the treatment information corresponds to health care services that are approved for payment, and
  determining whether the patient is a beneficiary of the carrier;
 program code means for initiating transmission of reply information to the client computers the reply information indicating to the health care provider whether the insurance claim is eligible for advance payment;
 program code means for initiating transmission of co-payment information to the client computer that indicates how much money the client owes as a co-payment for rendered health care services;
 program code means for performing, if the reply information indicates that the insurance claim is not in condition to be paid, the acts of:
  receiving a revised insurance claim; and
  determining whether the revised insurance claim is eligible for advance payment, wherein at least one of a diagnosis code or a treatment code included in the treatment information has been revised at the client computer; and
 program code means for performing, if the reply information indicates that the insurance claim is in condition to be paid, the acts of:
  transmitting claim information to the carrier for processing the claim;
  transmitting claim information to the payment entity for determining how much money to advance to the health care provider and for determining how to distribute the money prior to the carrier adjudicating the insurance claim to a first account accessible to the provider and a second account that is not accessible to the provider;
  debiting the second account for at least service fees;
  crediting any remaining money in the second account to the first account when the corresponding claim is adjudicated by the carrier;
  receiving financial information from the payment entity that indicates how much money will be advanced to the health care provider; and
  transmitting to the client system the financial information that indicates how much money will be advanced to the health care provider.

29. A computer program product as defined in claim 28, wherein the computer-executable instructions further comprise program code means for initiating transmission of a computer-displayable claim form to the client computer, the claim form including fields for accepting the patient information, insurance information, and treatment information.

30. A computer program product as defined in claim 29, wherein advance payment is payment that is received by the health care provider prior to receiving a payment from the carrier for the health care services that are the subject of the insurance claim.

31. A computer program product as defined in claim 30, wherein the advance payment is received by the health care provider prior to the carrier adjudicating the claim.

32. In a server system capable of communicating with a payment entity, a carrier, and a health care provider, a method of advancing payment for health care services rendered by the health care provide, the method comprising:
 receiving an insurance claim that includes patient information, insurance information, and treatment information from the provider;
 determining that the insurance claim is eligible for advance payment prior to receiving payment from the carrier by:
  determining that a patient is eligible for health care services;
  determining if the claim includes services that are approved for payment by the carrier; and
  comparing a diagnosis code and a treatment code with a compilation of accepted medical procedures to determine is the claim is eligible for advance payment; and
 transmitting claim information to a payment entity for distribution of an advance payment to an operational account that is accessible to the provider and a reserve account that is not accessible to the provider;
 distributing a first portion of the advance payment to the operational account and a second portion of the advance payment to the reserve account;
 debiting the reserve account for at least one of service fees, interest, or unpaid balances owed by the provider after the carrier makes payment for the insurance claims; and
 crediting a remaining amount in the reserve account to the operational account after the reserve account is debited for at least one of service fees, interest, or unpaid balances owed by the provider and after the carrier makes payment for the insurance claim.

* * * * *